US009078605B2

(12) United States Patent
Kissinger et al.

(10) Patent No.: US 9,078,605 B2
(45) Date of Patent: Jul. 14, 2015

(54) METHOD FOR FLUID COLLECTION FROM ANIMALS

(71) Applicants: Candice B. Kissinger, West Lafayette, IN (US); James M. Hampsch, Lafayette, IN (US); Joseph A. Bougher, Monticello, IN (US)

(72) Inventors: Candice B. Kissinger, West Lafayette, IN (US); James M. Hampsch, Lafayette, IN (US); Joseph A. Bougher, Monticello, IN (US)

(73) Assignee: Bioanalytical Systems, Inc., West Lafayette, IN (US)

( * ) Notice: Subject to any disclaimer, the term of this patent is extended or adjusted under 35 U.S.C. 154(b) by 7 days.

(21) Appl. No.: 14/148,236

(22) Filed: Jan. 6, 2014

(65) Prior Publication Data

US 2014/0121591 A1 May 1, 2014

Related U.S. Application Data

(62) Division of application No. 12/143,700, filed on Jun. 20, 2008, now Pat. No. 8,622,964, which is a division of application No. 10/612,484, filed on Jul. 2, 2003, now Pat. No. 7,488,309.

(60) Provisional application No. 60/393,816, filed on Jul. 3, 2002.

(51) Int. Cl.
*A61B 5/15* (2006.01)
*A61B 5/155* (2006.01)
*A61B 5/145* (2006.01)
*A61M 5/14* (2006.01)
*A61M 5/145* (2006.01)
*A61M 5/168* (2006.01)

(52) U.S. Cl.
CPC .............. *A61B 5/1427* (2013.01); *A61B 5/14* (2013.01); *A61M 5/1408* (2013.01); *A61M 5/1456* (2013.01); *A61M 5/16827* (2013.01); *A61M 2205/11* (2013.01); *A61M 2250/00* (2013.01)

(58) Field of Classification Search
CPC ..... A61B 5/1427; A61B 5/14; A61M 5/1408; A61M 5/1456; A61M 5/16827
USPC .......................... 604/131, 151, 191, 246, 256
See application file for complete search history.

(56) References Cited

U.S. PATENT DOCUMENTS

| 2,797,149 A | 6/1957 | Skeggs |
| 3,043,303 A | 7/1962 | Still |
| 3,630,417 A | 12/1971 | De Haas |
| 3,699,004 A | 10/1972 | Skeggs |
| 3,949,746 A * | 4/1976 | Wallach ................... 604/152 |
| 4,196,730 A | 4/1980 | Wilson |
| 4,340,153 A | 7/1982 | Spivey |
| 4,512,764 A | 4/1985 | Wunsch |
| 4,526,754 A | 7/1985 | Burns et al. |
| 4,559,036 A | 12/1985 | Wunsch |

(Continued)

OTHER PUBLICATIONS

International Searching Authority, International Search Report, Nov. 26, 2004.

*Primary Examiner* — Matthew F Desanto
(74) *Attorney, Agent, or Firm* — Ice Miller LLP

(57) ABSTRACT

A method for delivering a fluid to an animal with a drug delivery device without causing contamination to the drug delivery device. The drug delivery device used by the method may comprise a fluid subsystem with a switching device, disposable syringes, fluid reservoirs, disposable tubing, and a catheter. In one embodiment, the method allows a user to deliver multiple drugs to an animal without contaminating the valves that control the flow of fluid.

19 Claims, 8 Drawing Sheets

(56) References Cited

U.S. PATENT DOCUMENTS

| | | |
|---|---|---|
| 4,563,175 A | 1/1986 | LaFond |
| 4,666,429 A | 5/1987 | Stone |
| 4,666,430 A | 5/1987 | Brown et al. |
| 4,696,671 A | 9/1987 | Epstein et al. |
| 4,777,953 A | 10/1988 | Ash et al. |
| 4,784,157 A | 11/1988 | Halls et al. |
| 4,920,056 A | 4/1990 | Dasgupta |
| 5,037,390 A | 8/1991 | Raines et al. |
| 5,048,525 A | 9/1991 | Maxwell |
| 5,134,079 A | 7/1992 | Cusack et al. |
| 5,248,616 A | 9/1993 | Beckman et al. |
| 5,268,147 A | 12/1993 | Zabetakis et al. |
| 5,399,497 A | 3/1995 | Kumar et al. |
| 5,411,485 A | 5/1995 | Tennican et al. |
| 5,449,064 A | 9/1995 | Hogan et al. |
| 5,609,572 A | 3/1997 | Lang |
| 5,911,252 A | 6/1999 | Cassel |
| 6,062,224 A * | 5/2000 | Kissinger et al. ............ 128/897 |
| 6,102,897 A | 8/2000 | Lang |
| 6,150,119 A | 11/2000 | Kopf-Sill et al. |
| 6,187,529 B1 | 2/2001 | Fahy et al. |
| 6,193,667 B1 | 2/2001 | Kensey |
| 6,287,265 B1 | 9/2001 | Gleason |
| 6,767,319 B2 | 7/2004 | Reilly et al. |
| 6,794,197 B1 | 9/2004 | Indermuhle et al. |
| 2001/0031932 A1 * | 10/2001 | Blake et al. ................... 600/573 |
| 2004/0054320 A1 | 3/2004 | Kissinger et al. |

\* cited by examiner

FIRST PROCEDURE

| | | Refill syringe 1. Simultaneously check catheter. Then, flush catheter with sterile saline | | | | |
|---|---|---|---|---|---|---|
| Syringe 1 | Valve 1 | Syringe 2 | Valve 2 | Syringe 3 | Valve 3 | Valve 4 |
| PULL | Open to bag 1 (Saline) | STOPPED | Open to bag 2 | Pull until blood appears in catheter line | Open to Valve 2 and 4 | Open to Catheter |
| PUSH | Open to SYR 2 | STOPPED | Open to bag 2 | STOPPED | Open to Valve 2 and 4 | Open to Catheter |

SECOND PROCEDURE

| | | Refill syringe 1. Simultaneously check catheter. Flush catheter with sterile saline. Refill syringe 2 and flush with saline. | | | | |
|---|---|---|---|---|---|---|
| PULL | Open to bag 1 (saline) | STOPPED | Open to bag 2 | Pull until blood appears in catheter line | Open to Valve 2 and 4 | Open to Catheter |
| PUSH | Open to SYR 2 | STOPPED | Open to bag 2 | STOPPED | Open to Valve 2 and 4 | Open to Catheter |
| STOPPED | Open to bag 1 | PULL | Open to bag 2 | STOPPED | Open to bag 3 | Open to Catheter |
| STOPPED | Open to bag 1 | PUSH until fluid 2 reaches tee above valve 4, or until total volume of drug delivered | Open to valve 1 and 3 | STOPPED | Open to bag 3 | Open to Catheter |
| PUSH | Open to valve 2 | STOPPED (if drug delivered) | Open to bag 2 | STOPPED | Open to bag 3 | Open to Catheter |

FIG. 8

METHOD FOR FLUID COLLECTION FROM ANIMALS

CROSS-REFERENCE TO RELATED APPLICATIONS

This application is a division of U.S. patent application Ser. No. 12/143,700, filed Jun. 20, 2008, which is a division of U.S. patent application Ser. No. 10/612,484, filed Jul. 2, 2003, which issued as U.S. Pat. No. 7,488,309 B2 on Feb. 10, 2009, which claims the benefit of U.S. Provisional Application No. 60/393,816, filed Jul. 3, 2002.

FIELD

This disclosure relates to a method for delivery of fluids to animals, and, in particular, to a method for drug delivery thereto.

BACKGROUND

A syringe pump is a device which typically uses an electromechanical drive to advance and/or retract the plunger on a syringe mounted to that device. Syringe pumps perform multiple tasks in medical care and in biomedical research. Syringe pumps represent the most precise and reproducible means of delivering small volumes of fluid into the body or body tissues of animals. A catheter is a hollow, flexible tube, typically made from a biocompatible plastic, that can be inserted into a vein or artery in the body. For example in humans, the insertion procedure can take place quickly and with minimal discomfort if the vein is close to the skin and readily accessible. When the vein is close to the skin, a sharp needle is inserted into the vein and the catheter is inserted through the lumen (interior) of the needle until it exits the needle tip and enters the vein. The needle is then withdrawn, leaving the catheter tip positioned within the vein. The catheter is then secured to the skin to keep it in position.

After insertion, a catheter can be attached to a syringe and/or syringe pump, so that fluid can be delivered through it, or blood withdrawn from it. Examples of the types of fluids delivered to the body, for humans or various other animals, include physiological solutions such as saline (0.9% sodium chloride), Ringer's Solution, Ringer's Lactate Solution, or artificial cerebrospinal fluid. Such solutions can be administered alone, as in cases of dehydration or detoxification, or with supplements, including nutrients such as glucose, or therapeutic drugs intended to be delivered by parenteral administration (i.e. by the intravenous route). The administering and withdrawal of fluids from an animal can be controlled by the use of valves, or other like means for stopping or allowing fluid flow through the catheter. An example of a system that utilizes pinch valves, a syringe, a syringe pump and a catheter to withdraw blood and infuse saline is the Culex Automated Blood Sampling System manufactured by Bioanalytical Systems, Inc. of West Lafayette, Ind. US and disclosed in U.S. Pat. No. 6,062,224.

It is not atypical, especially during biomedical research with laboratory animals, to administer more than one type of fluid. The methods for making a change in solution include: (1) removing the syringe from the syringe pump and replacing it with another syringe filled with the new fluid; (2) removing, rinsing and refilling the syringe with the new solution; (3) inserting another catheter into another blood vessel and attaching another syringe pump to that blood vessel; or (4) attaching two syringe drives to some type of mechanism which allows the user to switch to the output between these drives. In example (4), the mechanism is often a two-way or three-way valve that is actuated by hand, by electric motor, or by a mechanical or electromechanical fluid switch device. Such mechanisms require that the fluid from both syringes pass into and through the device itself, exposing the fluid to the device and exposing the device to the fluid. Such exposure means that the device must be: (1) discarded after use; or (2) thoroughly cleaned between uses to avoid contamination leftover from prior experiments. Depending on the type of materials used in the switching device, it may not be possible to easily sterilize it between uses since not all materials are thermally stable, or resistant to the effects of sterilizing gases, radiation, or cold-sterilant fluids. Thus, it is desired to provide a device and method for delivery of solutions to animals that does not use a mechanism that exposes the switching device to the solution. Further, it is desired to provide a device and method for delivery of solutions that does not require manual operation or intervention.

In pharmaceutical research, with laboratory animals, new drugs in solution can be introduced into the body via a catheter into the bloodstream. This approach provides a means of controlling how much of the drug enters the body because the concentration of drug (e.g. milligrams per milliliter) in the solution will be known and the volume of drug delivered (e.g. milliliters) will be known. When a drug is administered by mouth, it is necessary to perform multiple tests to learn how much of that drug eventually enters the blood stream since there are several factors affecting absorption of the drug through the barrier represented by the gastrointestinal tract. When a drug solution is administered via a catheter, it can be described as a bolus dose, which is a relatively small volume of fluid administered over a relatively short period of time. In the rat, an example of a bolus dose would typically be a volume on the order of less than 3.0 milliliters and a time of less than 5 minutes. When a drug is administered as a bolus dose, its residence time in the body is determined by the rate at which the body can either metabolize it (e.g. via the liver) or excrete it (e.g. via the kidney or bile duct).

Another approach commonly followed is to administer a continuous infusion dose. In this scenario, the volume of fluid administered can be considerably larger, but the rate of flow is usually lower (e.g. less than 10 microliters per minute), and the length of the experiment can extend for several hours or days. When a drug is administered as a continuous dose, its residence time in the body reaches a steady state in which the rate of drug input (determined by flow rate of the syringe pump) is offset by the rate of drug metabolism and excretion.

These methods of delivering drugs to animals have several shortcomings. In many instances, a technician is required to manually introduce the drug into a solution for administration to the animal. Manual operation requires that the technician be present at all times that the drug(s) is(are) to be delivered. For a continuous infusion dose, constant attention by the technician is required to make certain that there is sufficient fluid remaining in the syringe or that the syringe is refilled without delay. Such use of human resources is expensive. Further, the accuracy of drug dose delivery is affected by the technician's skill and experience. Thus, accuracy may be compromised. Also, if more than one drug is to be administered, more than one technician may be required. These issues are further complicated by the need to change a solution and the shortcomings thereof as discussed herein. Therefore, it is desired to provide a device and method of drug delivery that does not require manual operation, is capable of delivery of more than one drug, does not contaminate the solution by requiring the solution to come into contact with a switching device that was exposed to another solution during a prior delivery, and permits for control of the amount and rate of flow of introduction of the drug(s) to the animal.

The need to deliver drugs for pharmaceutical testing purposes extends both to laboratory animals (such as mice, rats, guinea pigs, gerbils, monkeys, and pigs), as well, as humans. Thus, it is desirable that the device and method be useable for all "animals", where the term "animals" encompasses any mammals (including humans), reptiles, amphibians, or any other animal used for laboratory testing.

There also is a need to deliver fluids to animals other than through a catheter placed in a blood vessel. For example, a catheter or tube may be implanted into the stomach or duodenum of the animal. Thus, it is desired to provide a device and method for drug delivery to an animal that works in combination with all types of "catheters." As used herein, "catheter" refers to any type of tube connection to an animal's blood vessels and/or any type of tube connection that provides fluid (with or without a drug or drugs therein) to or extracts fluid from any part of the body, body tissues, organs, or blood system of the animal.

For purposes of understanding the effect of a drug on a subject, it is desirable to extract blood samples from an animal that has received the drug. Such samples are useful for a myriad of purposes, including, ascertaining the level of drug present in the blood stream of the animal at any time relative to the original introduction of that drug. Of course, it is also possible that extraction of other body fluids may be desired, such as in determining the level of drug in the bile, or the kidney, or the aqueous humor of the eye, or fluids in the lung, for example. In addition, there are other techniques for taking biological samples based on the use of dialysis probes that involve exchange of molecules but not fluids. Therefore, it is desired to provide a method of drug delivery for animals that works in conjunction with other equipment intended to extract fluid or dialyze molecules from the animal.

BRIEF SUMMARY

Exemplary embodiments relate to a device and a method for delivery and collection of fluids to and from animals and, in particular, to a device and method for drug delivery to animals. In one embodiment, the device comprises a drug delivery device that comprises a housing that holds a fluid subsystem and a first syringe pump, a second syringe pump and a third syringe pump. Each of the first, second and third syringe pumps are associated with a first, second and third syringe, respectively. The syringe pumps are associated with electronic controllers that control the push and/or pull operation of the first, second, and third syringes. The syringes are of the type often used for drug delivery and may be disposable. The fluid subsystem comprises a plurality of valves and plastic disposable tubing. In this embodiment, each valve is a two-position, pinch valve with two orifices that receive tubing. The orifices may be slots that make it easy to place the tubing in the valve without dismantling the fluid subsystem. Because each valve comprises a two-position, pinch valve, each orifice of the valve essentially comprises a first and second subvalve.

In this embodiment, each of the syringes are joined to a first, second or third fluid reservoir by a first syringe inlet, a second syringe inlet and a third syringe inlet, respectively. Each syringe inlet passes through the first subvalve of first, second and third pinch valves, respectively. Each of the first, second and third syringes are joined to each other by first, second and third syringe outlets that each pass through the second subvalve of the first, second, and third pinch valves, respectively. Further, the fluid subsystem is joined to a catheter by a catheter outlet that passes through a first subvalve of a fourth pinch valve. The fluid subsystem is also joined to a waste outlet that passes through the second subvalve of the fourth pinch valve.

One exemplary embodiment of the method for delivering fluids to and collecting fluids from an animal can utilize the drug delivery device to control the path of fluid(s) flowing through the fluid subsystem. The method operates the first, second and third syringe pumps to push or pull the first, second, and third syringes, and opens and closes the first and second subvalves of the first, second, third, and fourth pinch valves. The opening and closing of the subvalves determines what tubes are opened and closed to the flow of fluids and causes the drug delivery device to inject one or more fluids into an animal through a catheter without contamination. Further, the method may also collect fluid samples from the animal through the waste outlet.

BRIEF DESCRIPTIONS OF THE DRAWINGS

FIG. 8 shows tables of sample procedures using the exemplary embodiment of FIG. 1.

DESCRIPTION

Figure 1:
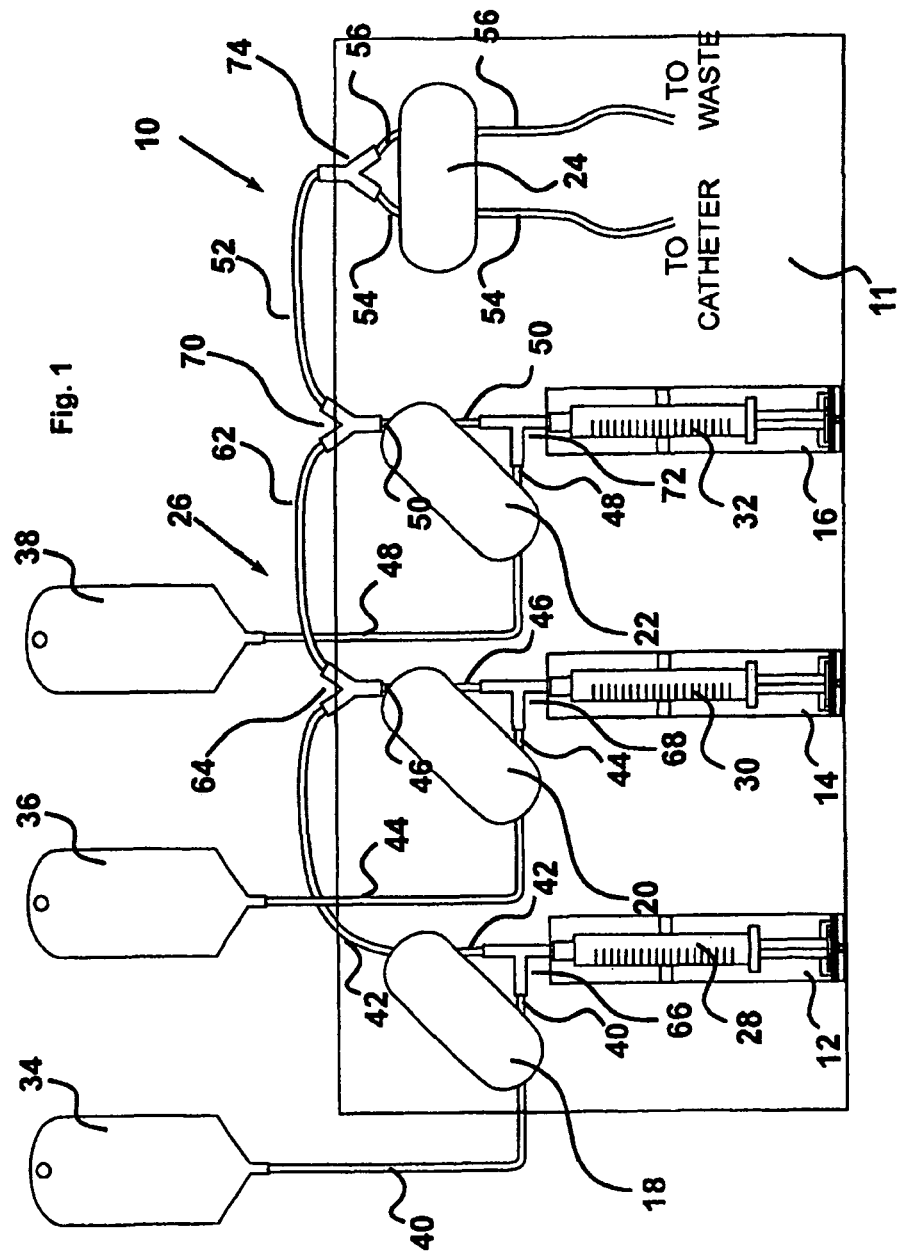
FIG. 1 shows a block diagram of one exemplary embodiment of the device.

Referring now to FIG. 1, there is shown a block diagram of one embodiment of the drug delivery device of the present disclosure. In this embodiment, a drug delivery device 10 includes a housing 11, a first syringe pump 12, a second syringe pump 14, a third syringe pump 16, a first valve 18, a second valve 20, a third valve 22, a fourth valve 24, and a fluid subsystem 26. Each of the first, second, and third syringe pumps 12, 14, and 16 have associated therewith electronic controllers (not shown) disposed within housing 11 for controlling the operation (push and pull) of a first syringe 28, a second syringe 30, and a third syringe 32. It will be appreciated by one skilled in the art that the electronic controllers can be disposed within housing 11 and a separate controller 114 or can be housed solely within the separate controller 114 (shown in FIG. 5). Such syringe pumps include, for example, the Empis pumps made by Bioanalytical Systems, Inc. of West Lafayette, Ind. US. First, second, and third syringes 28, 30, and 32 are of the type often used for drug delivery, and may be disposable. Such syringes include, for example, the 3 mL disposable luer syringes made by Becton Dickinson Corporation.

In this embodiment, the electronic control circuitry (not shown) for valves 18, 20, 22, and 24 are housed within housing 11. In addition, the electronic control circuitry may reside, in whole or in part, in separate controller 114 (shown in FIG. 5). In this embodiment, each of the valves 18, 20, 22, and 24 comprises a two-position, pinch valve with a first and second position that can each open and close. The first and second positions of each of the valves are orifices that receive disposable tubing. The orifices may be slots or other structures that make it easy to place the tubing in each valve without dismantling the fluid subsystem. Because each valve comprises a two-position, pinch valve, the orifice at the first position essentially comprises a first subvalve and the orifice at the second position essentially comprises a second subvalve. During operation, each valve's first position or second position will be open while the other position will be closed. The first position and second position cannot both be open or both be closed at the same time. While each position of each valve is either referred to as the first or second position, it will be appreciated by one skilled in the art that there is no difference between the two positions. Further, other means for stopping or allowing fluid flow will be obvious to those skilled in the art and are considered to be within the scope of the present disclosure.

Figure 2:
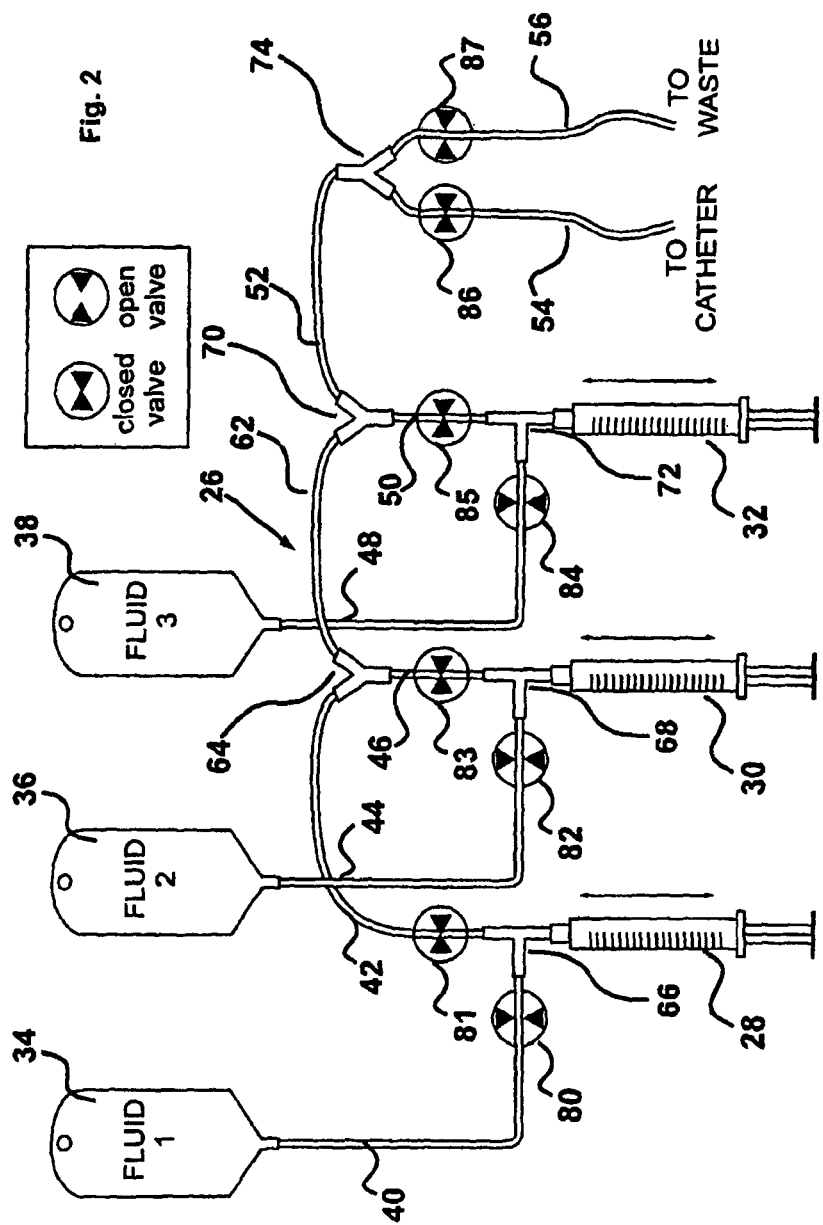
FIG. 2 shows a block diagram of the fluid subsystem utilized in the exemplary embodiment of FIG. 1.

FIG. 2 shows a block diagram of the fluid subsystem utilized in this exemplary embodiment. As shown in FIGS. 1 and 2, in this embodiment, first valve 18 comprises a first subvalve 80 and a second subvalve 81, second valve 20 comprises a first subvalve 82 and a second subvalve 83, third valve 22 comprises a first subvalve 84 and a second subvalve 85, and fourth subvalve 24 comprises a first subvalve 86 and a second subvalve 87. The electronic control circuitry controls the opening and closing of each of these subvalves. In operation, when the first subvalve (and hence the tube through the first subvalve) is open, the second subvalve is closed and, when the second subvalve (and hence the tube through the second subvalve) is open, the first subvalve is closed. Examples of two-position pinch valves used in the device of the present disclosure are the Empis Valve Assemblies made by Bioanalytical Systems, Inc.

Referring to FIGS. 1 and 2, fluid subsystem 26 includes first syringe 28, second syringe 30, third syringe 32, first valve 18, second valve 20, third valve 22, fourth valve 24, a first fluid reservoir 34, a second fluid reservoir 36, and a third fluid reservoir 38. First reservoir 34 is connected to first syringe 28 by a first syringe inlet 40 that passes through first subvalve 80 of valve 18. First syringe inlet 40 and syringe 28 are joined together by a first tee connector 66. Syringe 28 is connected to the rest of the fluid subsystem 26 by a first syringe outlet 42 that passes through second subvalve 81 of valve 18. Syringe outlet 42 and syringe 28 are also joined together by first tee connector 66. Further, syringe outlet 42 is connected to the rest of fluid subsystem 26 by a first y-connector 64.

Fluid reservoir 36 is connected to second syringe 30 by a second syringe inlet 44 that passes through first subvalve 82 of valve 20. Second syringe inlet 44 and syringe 30 are joined together by a second tee connector 68. Syringe 30 is connected to the rest of fluid subsystem 26 by a second syringe outlet 46 that passes through second subvalve 83 of valve 20. Second syringe outlet 46 and syringe 30 are also joined together by second tee connector 68. Further, syringe outlet 46 is connected to the rest of fluid subsystem 26 by first y-connector 64.

Fluid reservoir 38 is connected to third syringe 32 by a third syringe inlet 48 that passes through first subvalve 84 of valve 22. Third syringe inlet 48 and syringe 32 are joined together by a third tee connector 72. Syringe 32 is connected to the rest of fluid subsystem 26 by a third syringe outlet 50 that passes through the second subvalve 85 of valve 22. Third syringe outlet 50 and syringe 32 are also joined together by third tee connector 72. Further, third syringe outlet 50 is connected to the rest of fluid subsystem 26 by a second y-connector 70. Second y-connector 70 is connected to first y-connector 64 by a connecting tube 62. Y-connector 70 is also connected to a third y-connector 74 by a system outlet 52. Third y-connector 74 connects system outlet 52 to a catheter outlet 54 that passes through first subvalve 86 of valve 24 and to a waste outlet 56 that passes through second subvalve 87 of valve 24.

Each of the tee connectors and y-connectors have three receiving positions that can receive one of the tubes described above or one of the first, second and third syringes. While the tee connectors and y-connectors are shown as different structures in FIGS. 1-4, it will be appreciated by one skilled in the art that the tee connectors and y-connectors can be the same structure. Further, it will be appreciated by one skilled in the art that any type of connector can be used with the device, so long as the connectors in this embodiment have three receiving positions that can receive one of the tubes described above or one of the first, second and third syringes. Moreover, while the terms "inlet" and "outlet" are used herein to describe the tubing of fluid subsystem 26, such terms are not intended to be limiting as to the direction of fluid therethrough. Specifically, each "inlet" tube and each "outlet" tube supports bidirectional flow of fluid therethrough.

First, second, and third syringe pumps 12, 14, and 16 (see FIG. 1) are operable to push or pull first, second, and third syringes 28, 30, and 32, respectively. As previously mentioned, each of the subvalves 80, 81, 82, 83, 84, 85, 86, and 87 are electrically controlled as well. It will be appreciated by one skilled in the art that one of the subvalves associated with each syringe will be open at all times. Thus, any action by the syringe associated with that subvalve will affect the flow of fluid through that valve. Accordingly, drug delivery device 10 will be able to control the path of fluid(s) flowing through fluid subsystem 26 by controlling the subvalves and the syringes. To better understand the fluid subsystem, block diagrams of three alternate exemplary embodiments of the fluid subsystem are shown in FIGS. 2, 3, and 4.

For example, in FIG. 2, first subvalve 80 of first valve 18, first subvalve 82 of second valve 20, and first subvalve 84 of third valve 22 are all shown in the open position. If the plungers in first, second and third syringes 28, 30 and 32, respectively, are pulled out, then fluid residing in reservoirs 34, 36, and 38 will travel down syringe inlets 40, 44, and 48, respectively, to fill syringes 28, 30, and 32. The syringes 28, 30, and 32 could be activated in any order or any combination in order to be filled in this manner. In contrast, if second subvalve 81 of first valve 18, second subvalve 83 of second valve 20, and second subvalve 85 of third valve 22 were all open, then first subvalves 80, 82, and 84 would be closed. If this were the case, any action by syringe 28, 30, or 32 to expel the fluid contained inside that syringe would result in flow through the respective open second subvalve 81, 83, or 85. Again, syringes 28, 30, and 32 may be activated in any order or any combination in order to be emptied in this manner.

In FIG. 2, second subvalve 87 of fourth valve 24 is shown open, while first subvalve 86 of fourth valve 24 is closed. If any combination of second subvalves 81, 83, or 85 was open and any of syringes 28, 30, or 32 was emptied by pushing the syringes, then fluid would travel through the corresponding syringe outlet 42, 44, or 50 and through second subvalve 87 of fourth valve 24 to waste. If, in FIG. 2, first subvalve 86 of fourth valve 24 was open, then second subvalve 87 of fourth valve 24 would be closed. If any combination of second subvalves 81, 83, or 85 was open and any of syringes 28, 30, or 32 was emptied, then fluid would travel through the corresponding syringe outlet 42, 44, or 50 and through first subvalve 86 of fourth valve 24 to the catheter. Likewise, if any combination of first subvalves 81, 83, or 85 was open and the plunger on any of syringes 28, 30, or 32 was withdrawn, then fluid would travel from the catheter through first subvalve 86 of fourth valve 24 to line 52 and possibly through syringe outlets 42, 46, and 50 depending on the length of time the syringe was activated and the speed with which the plunger was withdrawn.

Figure 3:
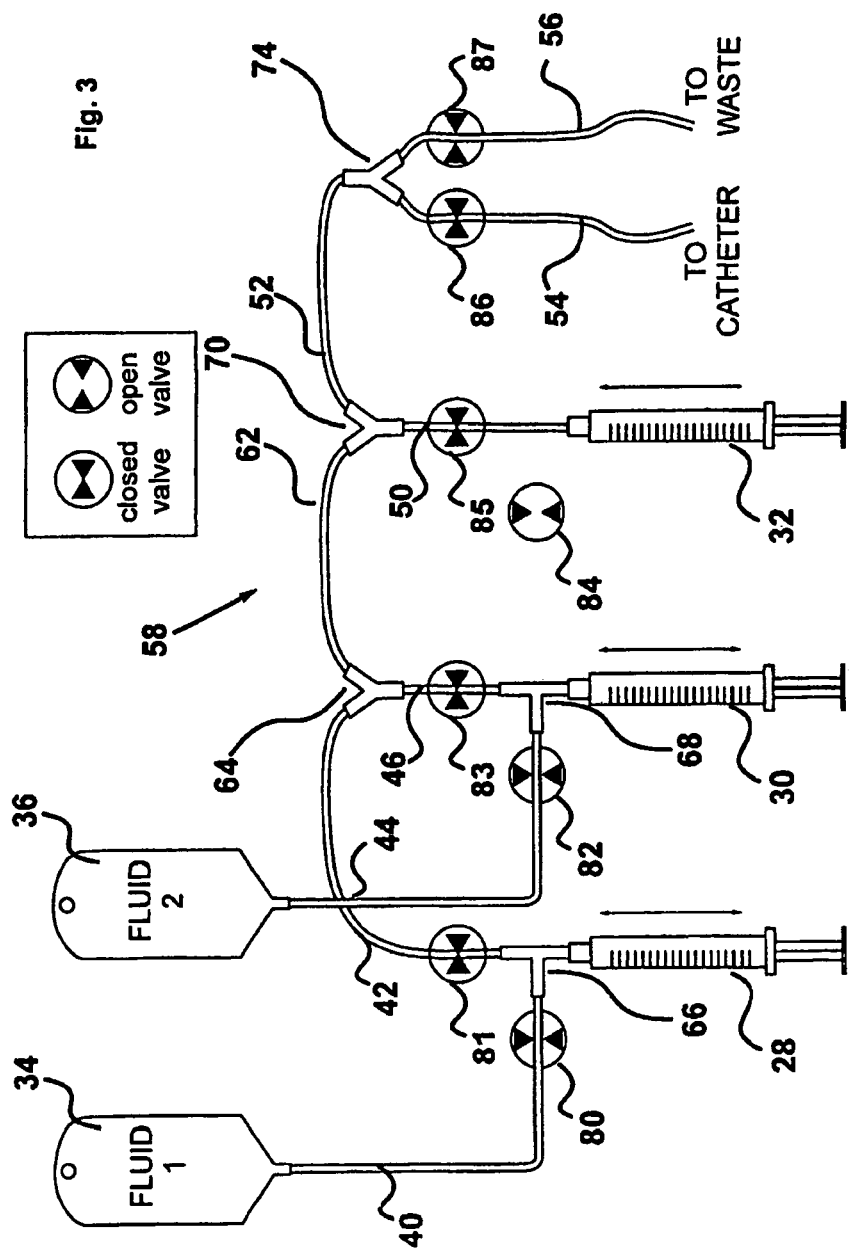
FIG. 3 shows a block diagram of another embodiment of the fluid subsystem shown in FIG. 2.
Figure 4:
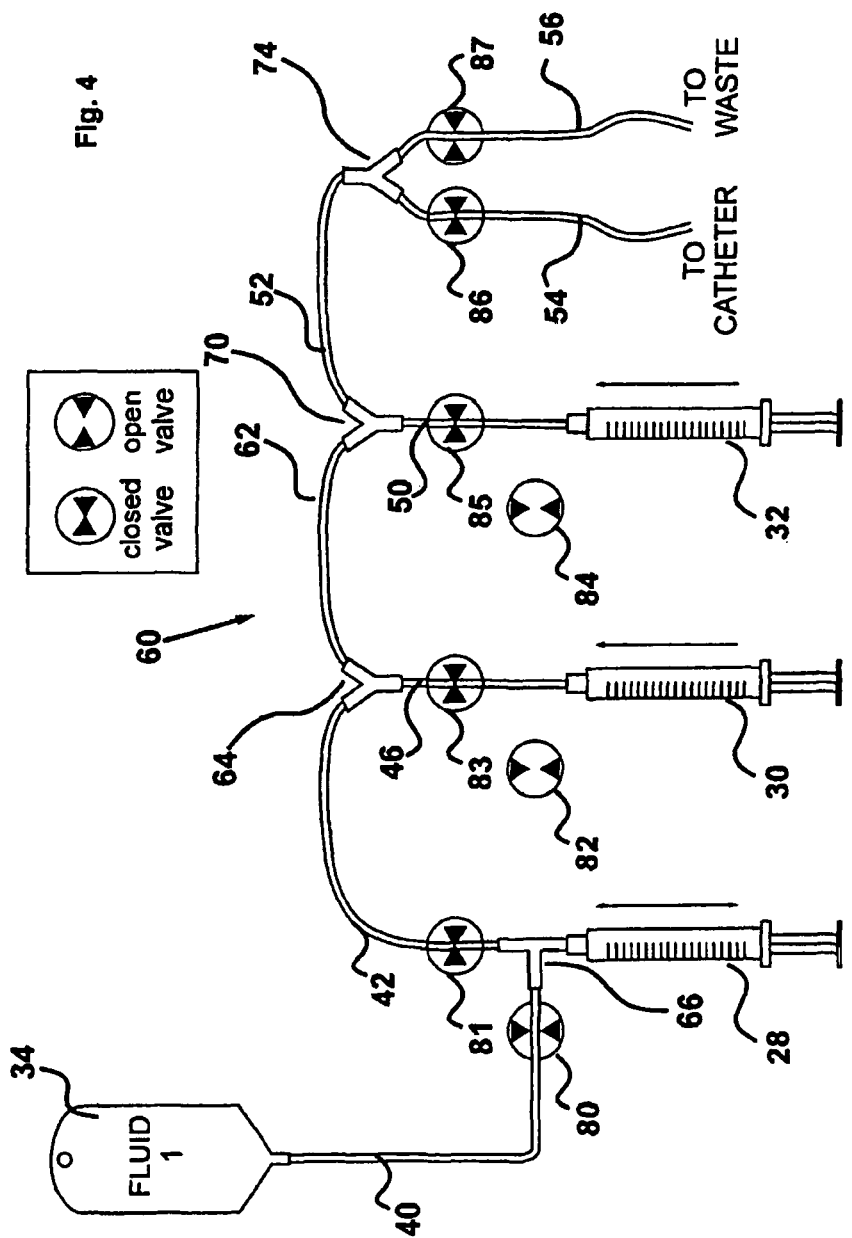
FIG. 4 shows a block diagram of a third embodiment of the fluid subsystem shown in FIG. 2.

FIG. 3 shows another exemplary embodiment of a fluid subsystem that can be utilized in the device. As shown in FIG. 3, this embodiment comprises a fluid subsystem 58 that has the same components of the previous embodiment except for third fluid reservoir 38 and third syringe inlet 48 (shown in FIG. 2) are not present. In this embodiment, third tee connector 72 (shown in FIG. 2) is not needed and third syringe outlet 50 is connected directly to third syringe 32. Hence, third syringe 32 cannot be refilled in this embodiment. Thus, third syringe 32 need only be operated by third syringe pump 16 (see FIG. 1) in a single direction (i.e., the push direction, to push fluid residing within third syringe 32 into third syringe outlet 50). Alternatively, third syringe pump 16 could still operate in both directions in order to pull the plunger while first subvalve 86 of fourth valve 24 was opened in order to allow fluid to pass from the catheter into fluid subsystem 58. Thus, syringe 32 could be used to pull fluid including blood or other fluid from the catheter. This embodiment may be useful in the event the particular solution of third syringe 32 is only needed in limited quantities, or when testing the catheter to make sure that it is not occluded by a blood clot or other biological obstacle. It is also useful in cases when there is a limitation on the amount of available drug and there is not sufficient material available to prepare a bag of solution as in fluid reservoir 34 or 36.

FIG. 4 shows another exemplary embodiment of the fluid subsystem of the present disclosure. This embodiment comprises fluid subsystem 60 and differs from the other embodiments because it only has one fluid reservoir, namely, first fluid reservoir 34. Thus, this embodiment does not have second fluid reservoir 36, third fluid reservoir 38, second syringe inlet 44, and third syringe inlet 48. Further, second and third tee connectors 68 and 72 are not needed. Accordingly, second syringe outlet 46 connects second syringe 30 directly to first y-connector 64 and third syringe outlet 50 connects third syringe 32 directly to y-connector 70.

In the embodiment of FIG. 4, second and third syringes 30 and 32 need only be operated by second and third syringe pumps 14 and 16 (see FIG. 1) in a single direction (i.e., the push direction in order to push fluid residing within second syringe 30 into second syringe outlet 46 and to push fluid residing within third syringe 32 into third syringe outlet 50). This embodiment may be useful in the event the particular solutions of second and third syringes 30 and 32 are only available in limited quantities, or when it is desirable to create a gradient in which the proportions of fluids in syringes 30 and 32 changes over time, increasing the proportion of one fluid relative to the other. It will also be appreciated by one skilled in the art that that the second and third syringe pumps 14 and 16 can operate to pull second syringe 30 and third syringe 32 to cause fluid to be drawn into second syringe outlet 46 and third syringe outlet 50 in order to collect a sample through the catheter from the animal.

The alternate embodiments of the fluid subsystem illustrate the flexibility of the fluid subsystem. While only three embodiments are shown and described, it will be appreciated by one skilled in the art that many other versions are possible and contemplated to be within the scope of this disclosure. For example, another embodiment can comprise a fluid system that has no fluid reservoirs connected to any of first, second and third syringes 28, 30 and 32. In this embodiment, syringe pumps 12, 14 and 16 operates syringes 28, 30 and 32 as described above in order to deliver fluids through the catheter outlet and/or waste outlet or to withdraw fluids from the catheter.

Figure 5:
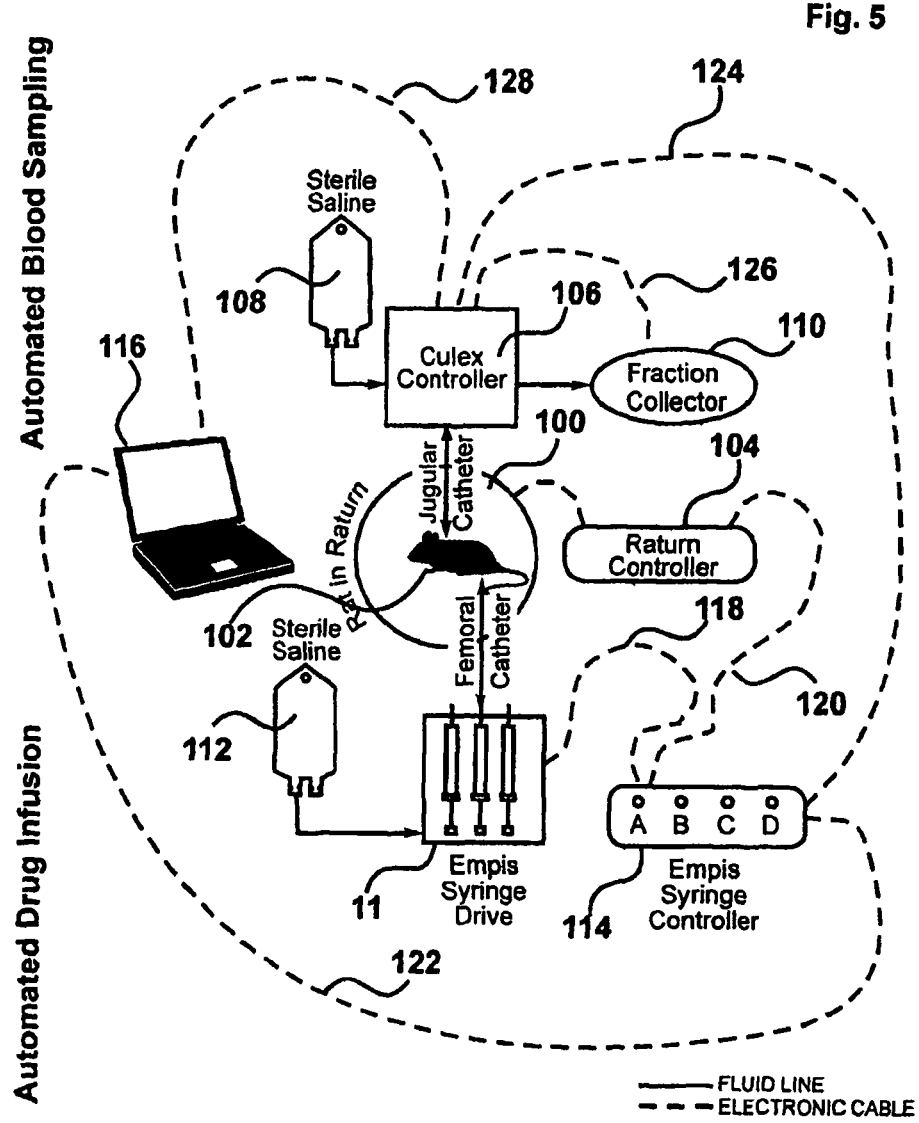
FIG. 5 shows a block diagram of the exemplary embodiment of FIG. 1 used together with a movement-responsive caging system and blood sampling system.

Referring now to FIG. 5, there is shown a block diagram of the device connected to a movement-responsive caging system and to a blood sampling system. The movement-responsive caging system is of the type disclosed in U.S. Pat. No. 5,816,256, and the blood sampling system of the type disclosed in U.S. Pat. No. 6,062,224. These U.S. patents are hereby incorporated herein by reference. As shown in FIG. 5, housing 11 of drug delivery device 10 is connected to a sterile saline reservoir 112. Sterile saline reservoir 112 is comparable to first fluid reservoir 34 shown in FIGS. 1-4. The movement-responsive caging system comprises a cage 100 having a rat 102 therein, and a controller 104. The blood sampling system includes a blood sampling controller 106, a sterile saline reservoir 108, and a fraction collector 110.

Referring still to FIG. 5, this exemplary embodiment also includes a processor 116 and a syringe controller 114. In this embodiment, syringe controller 114 contains the electrical power and control systems for control of the syringe pumps and the valves housed within housing 11. This arrangement differs from that of FIG. 1 in that the electronic control resides outside of housing 11. Housing 11 is electrically connected to syringe controller 114 by a syringe control line 118. Syringe controller 114 is also electrically connected to controller 104 of the movement-responsive caging system by a first line 120 and to processor 116 by a second line 122. The electrical connection between syringe controller 114 and controller 104 of the movement-responsive caging system is for the purpose of providing an alternate route for recording animal activity signals, including rotation, duration of rotation, rearing, and duration of rearing, when the test system comprises only the drug infusion device and the interactive caging system. Furthermore, syringe controller 114 is electrically connected to controller 106 of the blood sampling system by a third line 124. In this manner, communication is possible between the device, the movement-responsive caging system, and the blood sampling system.

In this embodiment, processor 116 provides a user interface for the device of the present disclosure and the blood sampling system. Processor 116 may comprise a personal computer, for example, having the WindoWS™ operating system and user interface program operating thereon. In addition to being connected by second line 122 to syringe controller 114, processor 116 is also electrically connected by a fifth line 128 to controller 106 of the blood sampling system. The electrical connection between controller 106 of the blood sampling system and processor 116 is for the purpose of sending instructions from the user interface software on processor 116 to an operational processor in controller 106, and for recording operational messages from controller 106 on the storage media of processor 116. Controller 106 is also connected to fraction collector 110 by a fourth line 126. It will be appreciated by one skilled in the art that lines 118, 120, 122, 124, 126 and 128 can comprise any type of electrical connections including, but not limited to, serial connection, parallel connection, use of a bus, ethernet, internet, Appletalk or other network, radio frequency, microwave, or Internet. The salient feature of each operative connection between these devices is that it is able to transmit and/or receive the data appropriate to the device at a speed sufficient for operational use of the device and in a manner that does not interfere with other devices in proximity to that device.

The use of the device with a movement-responsive caging system and blood sampling system permits for the sampling of blood of a freely moving animal (within the cage) while administering drug(s) to the animal. For example, in a typical experiment, the animal would be allowed to acclimate to the environment of the caging system for some period of time. During this time, a sample of blood would be taken to establish that no drug was present in the system prior to administration by drug delivery device 10. During this time, the animal activity would be monitored by processor 116 to establish a pre-dose pattern of activity. Then, drug delivery device 10 would be activated to deliver a predetermined volume of fluid from one or more syringes to the animal, and this would also trigger blood sampling to occur at predetermined intervals. Animal activity would be continuously recorded by processor 116 to monitor post-dose activity.

Figure 6:
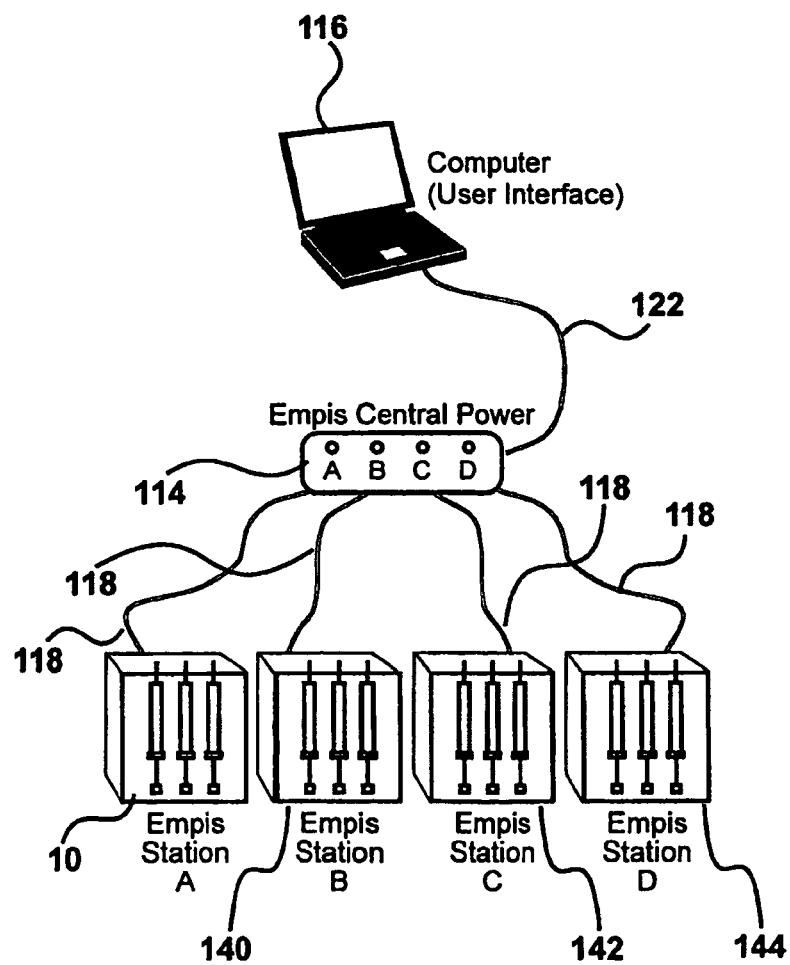
FIG. 6 shows a block diagram of one embodiment that utilizes multiple devices connected to a central processor.

Referring now to FIG. 6, there is shown a block diagram of one embodiment of multiple drug delivery devices 10, 140, 142 and 144 connected to a central processor 116. In this embodiment and the embodiment of FIG. 7, processor 116 comprises a computer. Further, in this embodiment, drug delivery devices 10, 140, 142 and 144 are all electrically connected to syringe controller 114 by syringe control lines 118. Further, controller 114 is electrically connected by line 122 to processor 116. In this embodiment, all four drug delivery devices 10, 140, 142, and 144 are controlled by controller 114. While this exemplary embodiment utilizes four drug delivery devices, it will be appreciated by one skilled in the art that any number of the drug delivery devices can be used.

Figure 7:
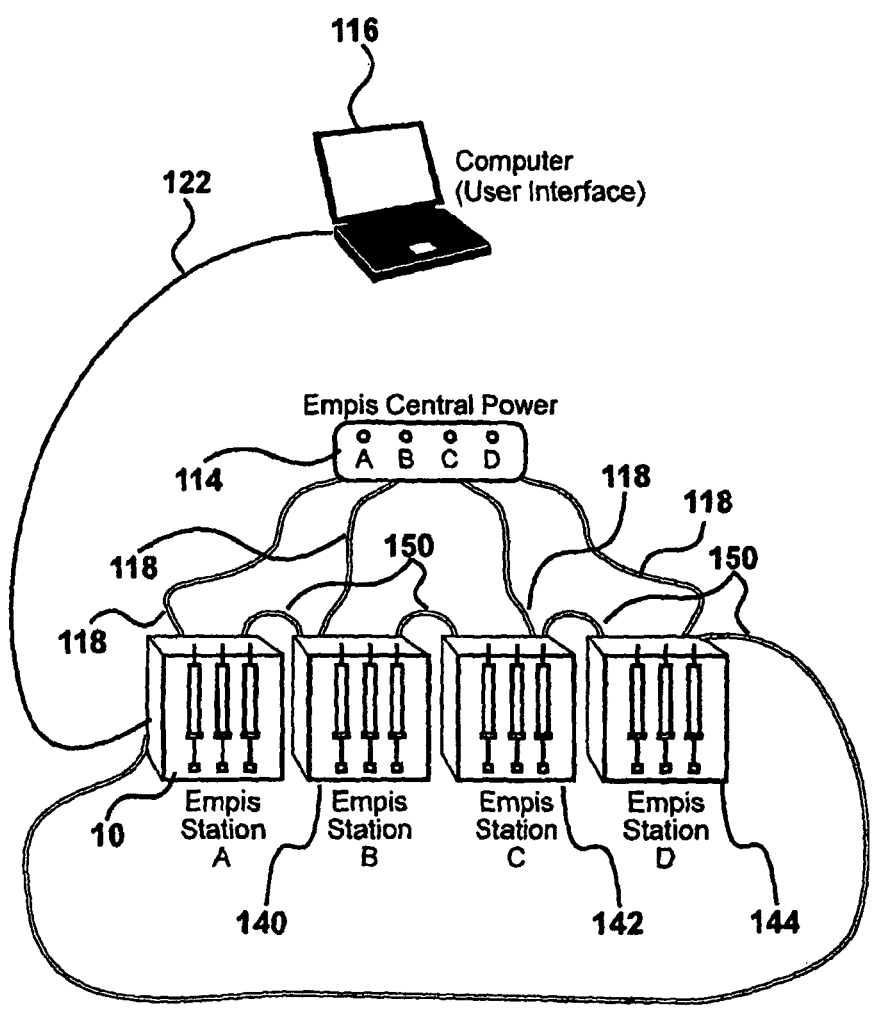
FIG. 7 shows a block diagram of another embodiment that utilizes multiple devices connected to a central processor.

It will also be appreciated by one skilled in the art that controller 114 could, alternatively, only provide a power source for drug delivery devices 10, 140, 142, and 144, while a processor within each of the drug delivery devices could provide the operational control for each device. Further, drug delivery devices 10, 140, 142 and 144 can form a network with one another and processor 116 while controller 114 serves as a power source. FIG. 7 shows a block diagram of an embodiment of multiple drug delivery devices 10, 140, 142 and 144 where the drug delivery devices are all connected to a network feeding back to processor 116. As shown in FIG. 7, drug delivery devices 10, 140, 142, and 144 are networked together by a plurality of wires 150. Further, drug delivery devices 10, 140, 142 and 144 are networked with processor 116 so that each drug delivery device in the network feeds back to processor 116. In this arrangement, the power supply would be isolated from possible damage by fluid leaks or spillage from drug delivery devices 10, 140, 142, and 144. The user interface for such control and for the results obtained with devices 10, 140, 142, and 144 is at processor 116. FIGS. 6 and 7 are further illustrative of the flexibility of the device. Multiple experiments or drug deliveries may be operated simultaneously and independently using these drug delivery devices. For example, the experimental protocol carried out on device 10 would not have to resemble the protocol carried out on any of the other devices 140, 142, or 144.

In two separate tables, FIG. 8 outlines two sample procedures using the exemplary embodiment of the drug delivery device of FIG. 1 and FIG. 2. In the first procedure of FIG. 8, a procedure is illustrated for checking a catheter and flushing the catheter with sterile saline. To illustrate one method to accomplish this objective, reference is made to the embodiment of FIG. 1 and FIG. 2. First syringe reservoir 34 (see FIG. 1) is filled with saline solution. Second syringe reservoir 36 and third syringe reservoir 38 are either empty or full. The catheter connected to catheter outlet 54 is implanted in a blood vessel, such as the jugular or femoral vein, of the animal.

To begin, first valve 18 is set to the position that opens subvalve 80 and allows fluid to pass through first syringe inlet 40. Second valve 20 is set to the position that opens subvalve 82 and allows fluid to pass through second syringe inlet 44. Third valve 22 is set to the position that opens subvalve 85 and allows fluid to pass through third syringe outlet 50. Fourth valve 24 is set to the position that opens subvalve 86 and allows fluid to pass through catheter outlet 54. First syringe 28 is pulled by first syringe pump 12, second syringe 30 is left stationary, and third syringe 32 is pulled by third syringe pump 16 until blood appears in catheter outlet 54. In this manner, first syringe 28 is filled with saline, while catheter outlet 54 is partially filled with blood to indicate that the catheter is not occluded by a clot, other biological obstacle, or kink in the catheter.

After first syringe 28 and third syringe 32 are pulled, first valve 18 is set to the position that opens subvalve 81 and allows fluid to pass through first syringe outlet 42. Third valve 22 is set to the position that opens subvalve 84. Second valve 20 remains open to second syringe inlet 44 and fourth valve 24 remains open to catheter outlet 54. Second and third syringes 30 and 32 remain stationary and first syringe is pushed by first syringe pump 12. In this manner, saline from syringe 28 is pushed through fluid subsystem 26 until it pushes blood out of catheter outlet 54 and back down the catheter. The catheter is now flushed and ready for introduction of one or more drugs.

In the second procedure of FIG. 8, a procedure is illustrated for flushing a catheter with sterile saline, refilling the second syringe, injecting fluid from the second syringe, and flushing with saline. This procedure outlines the sequence of events used to deliver a bolus injection of a drug. The procedure could be repeated with increasing concentrations of the drug as needed. To illustrate one method to accomplish this objective, reference is made to the exemplary embodiment of FIG. 1 and FIG. 2.

After the steps described above in association with the first procedure of checking a catheter and flushing the catheter with sterile saline, valve 18 is set to the position where subvalve 80 is open and allows fluid to pass through first syringe inlet 40. Valve 20 is set to the position that opens subvalve 82 and allows fluid to pass through second syringe inlet 44. Valve 22 is set to the position that opens subvalve 84 and allows fluid to pass through third syringe inlet 48. Valve 24 is set to the position that opens subvalve 86 and allows fluid to pass through catheter outlet 54. While third syringe 32 remains stationary, second syringe 30 is pulled by second syringe pump 14 until it fills with the fluid from second fluid reservoir 36 and first syringe 28 is pulled by first syringe pump 12 until it fills with saline from first fluid reservoir 34.

Next, valves 18, 22 and 24 remain in the same position while valve 20 is set to the position that opens subvalve 83 and allows fluid to pass through second syringe outlet 46. While first and third syringes remain stationary, second syringe 30 is then pushed until the total volume of the fluid is delivered. Fluid from reservoir 36 will normally comprise a drug that is desired to be tested. After the drug is delivered, valve 18 is set to the position where subvalve 81 is open and allows fluid to pass through first syringe outlet 42 and valve 20 is set to the position where subvalve 82 is open and allows fluid to pass through second syringe inlet 44. While second and third syringes 30 and 32 remain stationary, first syringe 28 is pushed by first syringe pump 12. In this manner, saline from syringe 28 is pushed through fluid subsystem 26 until the total volume of saline is delivered. In this manner, drug delivery device 10 flushes the fluid subsystem 26 and the catheter. The catheter is now flushed and ready for introduction of one or more other drugs. As will be appreciated by those of skill in the art, there are additional procedures that could be achieved by the device. Other examples include situations such as delivery of a bolus injection (loading dose) followed by continuous delivery of a drug from a refillable syringe (continuous infusion).

This embodiment and procedure enables the drug delivery device to flush saline, or another like fluid, down the catheter to keep the catheter from becoming occluded by other fluids, such as clotted blood. The volume of saline and the interval for this flushing can be preprogrammed. The flushing will occur as described above in association with FIGS. 1 and 2, but will also keep subvalve 81 of valve 18 closed momentarily while syringe pump 12 begins to push syringe 28. In this way, drug delivery device 10 begins to build up pressure. Once subvalve 81 is open and allows fluid to pass through first syringe outlet 42 the pressure behind the flushing saline will blow out any clots forming in the catheter.

It will be appreciated by those of skill in the art that these embodiments of the device and method meets the specific needs of drug delivery, because they utilize multiple disposable syringes that can be easily replaced with clean and sterile syringes. Further, each syringe is independently programmable, with start, stop, direction and flow rate independent of the others, so that one syringe may run while the other syringe(s) is(are) stopped, or two syringes may run while the other syringe(s) is(are) stopped, or all syringes may run together, or none may run, during any programmed sequence. The independent control for each of these syringes conserves the fluid in the syringes until the syringes are activated. Moreover, each syringe can be automatically refillable from independent reservoirs of drug solution, when connected to those reservoirs.

The fluid reservoirs and syringes are connected together into a single fluid subsystem, by means of sterile, disposable plastic tubing, tee connectors and y-connectors. Accordingly, fluid remains in the syringes, sterile tubing and fluid reservoirs and does not exit the fluid subsystem or contaminate other components, such as the valves that control the flow of fluid. Further, the syringes, sterile tubing and sterile reservoirs are immediately accessible by the user and can be replaced with ease. The fluid subsystem is connected to a catheter attached to an animal, including, but not limited to, a catheter implanted into a blood vessel. It will be appreciated by one skilled in the art that this fluid subsystem can be connected to any type of catheter, including catheters not used in blood vessels. For example, the fluid subsystem can be connected to a tube implanted into the stomach or duodenum of an animal.

Each syringe can be used to deliver fluids to or collect fluids from an animal. Each syringe pump is reversible (i.e. can be used to pull as well as push). Thus, these embodiments can take samples by pulling a syringe to extract fluid past the last valve, into one of the syringes and, subsequently, by pushing the syringe to force the extracted fluid out the waste outlet for collection. Switching among the contents of the syringes is achieved by the position of valves associated with each syringe. The position of the valves either allow the fluid to be delivered to or collected from the catheter by a syringe or allows a syringe to be bypassed by the collected or delivered fluid.

Thus, these embodiments can be programmed to deliver a desired volume of fluid from one or multiple syringes into a single catheter without that fluid being exposed to any component which is not part of either the disposable tubing, tee connectors, y-connectors or syringes that comprise the fluid subsystem. These embodiments also provide for a mechanism for flushing fluid through the fourth valve either to the catheter or to the waste outlet in order to reduce the total volume of fluid flowing to the catheter after a syringe change has been initiated. In one embodiment, one syringe can be dedicated to providing a periodic flush and to ensure that the catheter is kept filled with a sterile solution, such as saline, to prevent the catheter from becoming occluded by other fluids, such as clotted blood, when used in connection with a catheter implanted in a blood vessel of the animal.

While the device and method of the present disclosure have been described in considerable detail with references to particular embodiments thereof, such is offered only by way of non-limiting examples of embodiments of the device and methods as many other versions are possible. It is anticipated that a variety of other modifications and changes will be apparent to those having ordinary skill in the art and that such modifications and changes are intended to be encompassed with the spirit and scope of the pending claims.

We claim:

1. A method for collecting fluids from an animal, the method comprising the steps of:
   a. providing a waste outlet and a catheter;
   b. inserting the catheter into the animal, so that a fluid can be withdrawn from the animal;
   c. connecting the catheter and the waste outlet to at least one fluid collection device having:
      i. a system output operably connected to the waste outlet and the catheter;
      ii. a first, second, and third tubes;
      iii. a first syringe with a first syringe inlet and a first syringe outlet, and a second syringe with a second syringe inlet and a second syringe outlet, wherein the second syringe inlet is operably connected via the first tube to the first syringe outlet, wherein the second syringe outlet is operably connected to the system output by the second tube, and wherein the first tube is operably connected to the second tube;
      iv. a first fluid reservoir with a first fluid, wherein the first fluid reservoir is connected to the first syringe by the third tube operably connected to the first syringe inlet and the first fluid reservoir, and wherein the third tube is operably connected to the first tube; and
      v. a first valve that has a first position and a second position that is operably connected to the third tube and controls fluid flow between the first fluid reservoir and the first syringe, a second valve that has a first position and a second position that is operably connected to the first tube and controls fluid flow between the first syringe and either the first fluid reservoir, the second syringe or the system output, and a third valve that has a first position and a second position that is operably connected to the second tube and controls fluid flow between the second syringe and either the first syringe or the system output;
   d. withdrawing a fluid sample from the animal into the second syringe by opening the second position of the second valve, opening the first position of the third valve and pulling the second syringe, so that the fluid sample will pass through the catheter into the system output of the fluid collection device and into the second syringe; and
   e. collecting the fluid sample by opening the second position of the third valve and pushing the second syringe, so that the fluid sample will pass out of the system output of the fluid collection device through the waste outlet.

2. The method of claim 1, wherein the fluid collection device further comprises a fourth tube and a third syringe including a third syringe inlet and a third syringe outlet that is operably connected via the fourth tube to the first syringe by the first syringe inlet and the third syringe outlet.

3. The method of claim 2, wherein the fluid collection device further comprises a fifth tube and a second fluid reservoir filled with a second fluid, wherein the third syringe is operably connected via the fifth tube to the second fluid reservoir by the third syringe inlet, and wherein the fifth tube is operably connected to the fourth tube.

4. The method of claim 3, further comprising the steps of:
(d) filling the first syringe with the first fluid from the first fluid reservoir by opening the first position of the first valve and pulling the first syringe so that the first fluid flows through the first syringe inlet into the first syringe;
(e) delivering the first fluid to the animal by opening the second position of the first valve, opening the first position of the third valve, and pushing the first syringe, so that the first fluid will pass through the system output of the fluid collection device and into the catheter;
(f) withdrawing a fluid sample from the animal into the second syringe by opening the second position of the second valve, opening the first position of the third valve and pulling the second syringe, so that the fluid sample will pass through the catheter into the system output of the fluid collection device and into the second syringe; and
(g) collecting the fluid sample by opening the second position of the third valve and pushing the second syringe, so that the fluid sample will pass out of the system output of the fluid collection device through the waste outlet.

5. The method of claim 4, wherein the fluid collection device further comprises a fourth valve that has a first position and a second position that is operably connected to the fifth tube and controls fluid flow between the second fluid reservoir and the third syringe.

6. The method of claim 5, further comprising the steps:
(h) filling the third syringe with the second fluid from the second fluid reservoir by opening the first position of the fourth valve and pulling the third syringe so that the third fluid flows through the third syringe inlet into the third syringe; and
(i) flushing the fluid collection device by pushing and pulling the first, second, and third syringes to cause the third fluid to pass through the first, second, and third syringes and so that the first fluid will pass out of the system output of the fluid collection device through the waste outlet.

7. The method of claim 6, further comprising a first syringe pump associated with the first syringe, a second syringe pump associated with the second syringe, and a third syringe pump associated with the third syringe, such that steps (d)-(i) comprise using the first, second, and third syringe pumps to push and pull the first, second, and third syringes.

8. The method of claim 3, wherein the fluid collection device further comprises a fourth valve that has a first position and a second position that is operably connected to the fifth tube and controls fluid flow between the second fluid reservoir and the third syringe, and further comprises a fifth valve that has a first position and a second position that is operably connected to the fourth tube and controls fluid flow between the third syringe and either the second fluid reservoir, the first syringe, the second syringe, or the system output.

9. The method of claim 8, wherein the fluid collection device further comprises a sixth valve that has a first position and a second position that is operatively connected to the waste outlet, so that when the first position of the sixth valve is open, the second position of the sixth valve is closed and fluid is allowed to pass between the system output and the catheter, and when the second position of the sixth valve is open, the first position of the sixth valve is closed and fluid is allowed to pass between the system output and the waste outlet.

10. The method of claim 2, further comprising the step of pulling the second syringe and the third syringe to cause fluid to be drawn into the second syringe and the third syringe in order to collect a sample through the catheter from the animal.

11. The method of claim 1, wherein the fluid collection device further comprises a fourth tube and a third syringe including a third syringe inlet and a third syringe outlet that is filled with a second fluid and that is operably connected via the second tube to the second syringe by the second syringe outlet and the third syringe inlet, wherein the third syringe outlet is operably connected via the fourth tube to the system output, and wherein the fourth tube is operably connected to the second tube.

12. The method of claim 11, wherein the fluid collection device further comprises a fourth valve that has a first position and a second position that is operably connected to the fourth tube and controls fluid flow between the third syringe and the second syringe or the system output.

13. The method of claim 12, further comprising the step of:
(f) flushing the fluid collection device with the second fluid from the third syringe by closing the second position of the second valve, opening the second position of the fourth valve, and pushing the third syringe using the third syringe pump so that the second fluid will pass out of the system output of the fluid collection device through the waste outlet.

14. The method of claim 11, wherein the fluid collection device further comprises a second syringe pump operably connected to the first syringe and a third syringe pump operably connected to the third syringe, wherein each of the first, second, and third syringe pumps operate independently of one another.

15. The method of claim 1, further comprising the step of filling the first syringe with the fluid from the first fluid reservoir by opening the first position of the first valve and pulling the first syringe.

16. The method of claim 1, wherein the fluid collection device further comprises a first syringe pump associated with second syringe, such that step (d) comprises using the first syringe pump to pull the second syringe and step (e) comprises using the first syringe pump to push the second syringe.

17. The method of claim 1, further comprising the steps of:
(f) filling the first syringe with the first fluid from the first fluid reservoir by opening the first position of the first valve and pulling the first syringe so that the first fluid flows through the first syringe inlet into the first syringe; and
(g) flushing the fluid collection device by pushing and pulling the first syringe and the second syringe to cause the first fluid to pass through the first syringe outlet and the second syringe outlet so that the first fluid will pass out of the system output of the fluid collection device through the waste outlet.

18. The method of claim 17, further comprising a second syringe pump associated with the first syringe, such that step (f) comprises using the second syringe pump to pull the first syringe and step (g) comprises using the first and second syringe pumps to push and pull the first and second syringes.

19. The method of claim 16, wherein the fluid collection device further comprises a controller that is operably connected to the first syringe pump and that is operably connected to the second and third valves, such that in steps (d) and (e) the controller automatically controls the movement of the first syringe pump and controls the movement of the first and second positions of the second and third valves.

* * * * *